(12) United States Patent
Liu et al.

(10) Patent No.: US 11,160,466 B2
(45) Date of Patent: Nov. 2, 2021

(54) HEART RATE CORRECTION FOR RELATIVE ACTIVITY STRAIN

(71) Applicant: Microsoft Technology Licensing, LLC, Redmond, WA (US)

(72) Inventors: Zongyi Liu, Issaquah, WA (US); Haithem Albadawi, Redmond, WA (US); Shunan Li, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 165 days.

(21) Appl. No.: 15/013,912

(22) Filed: Feb. 2, 2016

(65) Prior Publication Data
US 2017/0095169 A1 Apr. 6, 2017

Related U.S. Application Data

(60) Provisional application No. 62/237,421, filed on Oct. 5, 2015.

(51) Int. Cl.
*A61B 5/024* (2006.01)
*A61B 5/00* (2006.01)
*A61B 5/11* (2006.01)

(52) U.S. Cl.
CPC .......... *A61B 5/02416* (2013.01); *A61B 5/681* (2013.01); *A61B 5/721* (2013.01); *A61B 5/1118* (2013.01)

(58) Field of Classification Search
CPC . A61B 5/1118; A61B 5/0205; A61B 5/02405; A61B 5/486; A61B 5/7264;
(Continued)

(56) References Cited

U.S. PATENT DOCUMENTS 5,243,993 A 9/1993 Alexander et al.
6,135,951 A 10/2000 Richardson et al.
(Continued)

FOREIGN PATENT DOCUMENTS

CN 104207756 A 12/2014
CN 104921702 A 9/2015
(Continued)

OTHER PUBLICATIONS

ISA European Patent Office, International Search Report and Written Opinion Issued in PCT Application No. PCT/US2016/054031, dated Dec. 21, 2016, WIPO, 11 pages.
(Continued)

*Primary Examiner* — Deborah L Malamud
(74) *Attorney, Agent, or Firm* — Alleman Hall Creasman & Tuttle LLP

(57) ABSTRACT

A wearable heart rate monitoring device includes an optical sensor configured to translate test light reflected from a wearer of the wearable heart rate monitoring device into a machine-readable heart rate signal. The wearable heart rate monitoring device also includes an elevation sensor configured to translate an elevation of the wearable heart rate monitoring device into a machine-readable elevation signal. The wearable heart rate monitoring device further includes a heart rate reporting machine configured to output an estimated heart rate based on at least the machine-readable heart rate signal and the machine-readable elevation signal.

13 Claims, 7 Drawing Sheets

(58) Field of Classification Search
CPC ..... A61B 5/024; A61B 5/0006; A61B 5/0245; A61B 5/0402; A61B 5/1124; A61B 5/0255; A61B 5/04012; A61B 5/05; A63B 24/0062; A63B 2024/0068; A63B 2230/06; G06F 19/322; G06F 19/3418; G06F 19/345; G06K 9/00342; G06K 2009/00939; Y10S 482/901

See application file for complete search history.

(56) References Cited

U.S. PATENT DOCUMENTS

| | | | |
|---|---|---|---|
| 6,334,065 | B1 | 12/2001 | Al-Ali et al. |
| 6,905,470 | B2 | 6/2005 | Lee et al. |
| 8,475,370 | B2 | 7/2013 | McCombie et al. |
| 8,583,402 | B2 | 11/2013 | Yuen et al. |
| 8,827,906 | B2 | 9/2014 | Yuen et al. |
| 8,961,415 | B2 | 2/2015 | LeBoeuf et al. |
| 2006/0111623 | A1 | 5/2006 | Stetson |
| 2008/0255436 | A1 | 10/2008 | Baker |
| 2009/0112111 | A1 | 4/2009 | Shimizu et al. |
| 2010/0113948 | A1 | 5/2010 | Fang et al. |
| 2012/0083705 | A1 | 4/2012 | Yuen et al. |
| 2012/0190948 | A1 | 7/2012 | Vetter et al. |
| 2014/0058217 | A1 | 2/2014 | Giovangrandi |
| 2014/0058272 | A1 | 2/2014 | Naing et al. |
| 2014/0121540 | A1* | 5/2014 | Raskin ................ A61B 5/6898 600/479 |
| 2014/0213858 | A1 | 7/2014 | Presura et al. |
| 2014/0213863 | A1 | 7/2014 | Loseu et al. |
| 2014/0275854 | A1 | 9/2014 | Venkatraman et al. |
| 2014/0278139 | A1* | 9/2014 | Hong .................. A61B 5/4866 702/19 |
| 2014/0316305 | A1 | 10/2014 | Venkatraman et al. |
| 2015/0080746 | A1 | 3/2015 | Bleich et al. |
| 2015/0196256 | A1 | 7/2015 | Venkatraman et al. |
| 2017/0095169 | A1 | 4/2017 | Liu et al. |

FOREIGN PATENT DOCUMENTS

| | | |
|---|---|---|
| KR | 20030081903 A | 10/2003 |
| KR | 100763233 B1 | 10/2007 |
| KR | 20110088644 A | 8/2011 |
| WO | 2015069124 A1 | 5/2015 |
| WO | 2015087164 A1 | 6/2015 |
| WO | 2015102589 A1 | 7/2015 |
| WO | 2015139930 A1 | 9/2015 |

OTHER PUBLICATIONS

Couceiro, et al., "Detection of Motion Artifacts in Photoplethysmographic Signals based on Time and Period Domain Analysis", In Proceedings of 34th Annual International Conference of the IEEE Engineering in Medicine and Biology Society, Aug. 28, 2012, pp. 2603-2606.

Yousefi, et al., "Adaptive Cancellation of Motion Artifact in Wearable Biosensors", In Proceedings of 34th Annual International Conference of the IEEE Engineering in Medicine and Biology Society, Aug. 28, 2012, pp. 2004-2008.

Zhang, et al., "Troika: A General Framework for Heart Rate Monitoring Using Wrist-Type Photoplethysmographic Signals during Intensive Physical Exercise", In Proceedings of IEEE Transactions on Biomedical Engineering, vol. 62, Issue 2, Feb. 2015, pp. 522-531.

Zhang, Zhilin, "Heart Rate Monitoring From Wrist-Type Photoplethysmographic (Ppg) Signals During Intensive Physical Exercise", In Proceedings of IEEE Global Conference on Signal and Information Processing, Dec. 3, 2014, pp. 698-702.

Kan, Y et al., "An Efficient Motion-Resistant Method for Wearable Pulse Oximeter," IEEE Transactions of Information Technology in Biomedicine, vol. 12, No. 3, May 2008, 7 pages.

Peng, F et al., "A comb filter based signal processing method to effectively reduce motion artifacts from photoplethysmographic signals," Physiological Measurement, vol. 36, No. 10, Oct. 2015, Published Online Sep. 3, 2015, 12 pages.

IPEA European Patent Office, Second Written Opinion Issued in PCT application No. PCT/US2016/054031, dated Aug. 18, 2017, WIPO, 6 pages.

"First Office Action and Search Report Issued in Chinese Patent Application No. 201680058144.X", dated Mar. 27, 2020, 17 Pages.

* cited by examiner

HEART RATE CORRECTION FOR RELATIVE ACTIVITY STRAIN

CROSS REFERENCE TO RELATED APPLICATIONS

This application claims priority to U.S. Provisional Patent Application No. 62/237,421, filed on Oct. 5, 2015, the entirety of which is hereby incorporated herein by reference.

BACKGROUND

Many people find it helpful and informative to track their own heart rate, in particular during periods of exercise. A variety of wearable devices exist which are usable for tracking heart rate.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A wearable heart rate monitoring device includes an optical sensor configured to translate test light reflected from a wearer of the wearable heart rate monitoring device into a machine-readable heart rate signal. The wearable heart rate monitoring device also includes an elevation sensor configured to translate an elevation of the wearable heart rate monitoring device into a machine-readable elevation signal. The wearable heart rate monitoring device further includes a heart rate reporting machine configured to output an estimated heart rate based on at least the machine-readable heart rate signal and the machine-readable elevation signal.

DETAILED DESCRIPTION

A common function of wearable electronic devices is the measurement of wearer heart rate. However, many techniques for heart rate measurement are susceptible to signal contamination, compromising the accuracy of the measured heart rate. For example, during activity, a measured heart rate signal may be contaminated by a motion (e.g., footfalls, wrist movements, etc.) of the wearer of the wearable heart rate monitoring device, as well as ambient light, and/or other potential sources of signal noise.

Techniques exist which are usable to mitigate motion contamination in a heart rate signal, potentially returning a more accurate heart rate measurement. For example, some techniques involve detecting a mean heart rate over a period of time, and comparing new heart rate estimates to the calculated mean. Any new estimates which differ from the mean by more than a threshold value are discarded as outliers and not reported to the wearer. This may serve to provide more accurate heart rate measurements to wearable heart rate monitoring device users during periods of acute signal contamination.

However, in some cases, the heart rate of a wearer of a heart rate monitoring device may abruptly change, deviating from a previously calculated heart rate mean. For example, when a wearer begins moving uphill, the wearer's heart rate may begin to rapidly climb. New, accurate heart rate measurements may be compared to the calculated mean heart rate and discarded as outliers, thereby resulting in an inaccurate heart rate estimate.

Accordingly, the present disclosure is directed toward a technique for correcting a heart rate signal based on a perceived strenuousness of an activity performed by the wearer of the wearable heart rate monitoring device. First, a first candidate heart rate is estimated using a first heart rate estimation approach. The first heart rate estimation approach may include motion-correcting a machine-readable heart rate signal, and evaluating crossings of a z-axis in order to estimate the first candidate heart rate. A series of estimated heart rates may be used to calculate a mean heart rate. Next, a machine-readable activity-strain signal is used to evaluate a relative strenuousness of the activity which the wearer is currently performing. If the first candidate heart rate is found to be consistent with the machine-readable activity-strain signal, it is output for further processing and/or display to the wearer. If it is determined that the first candidate heart rate is inconsistent with the activity-strain signal, a second estimation approach is used to estimate a second candidate heart rate, which is then output for further processing and/or display to the wearer. The second estimation approach may include identifying a highest occurrence frequency in a frequency search window of a frequency domain representation of the machine-readable heart rate signal. The frequency search window may be centered on the previously calculated mean heart rate.

Figure 1A:
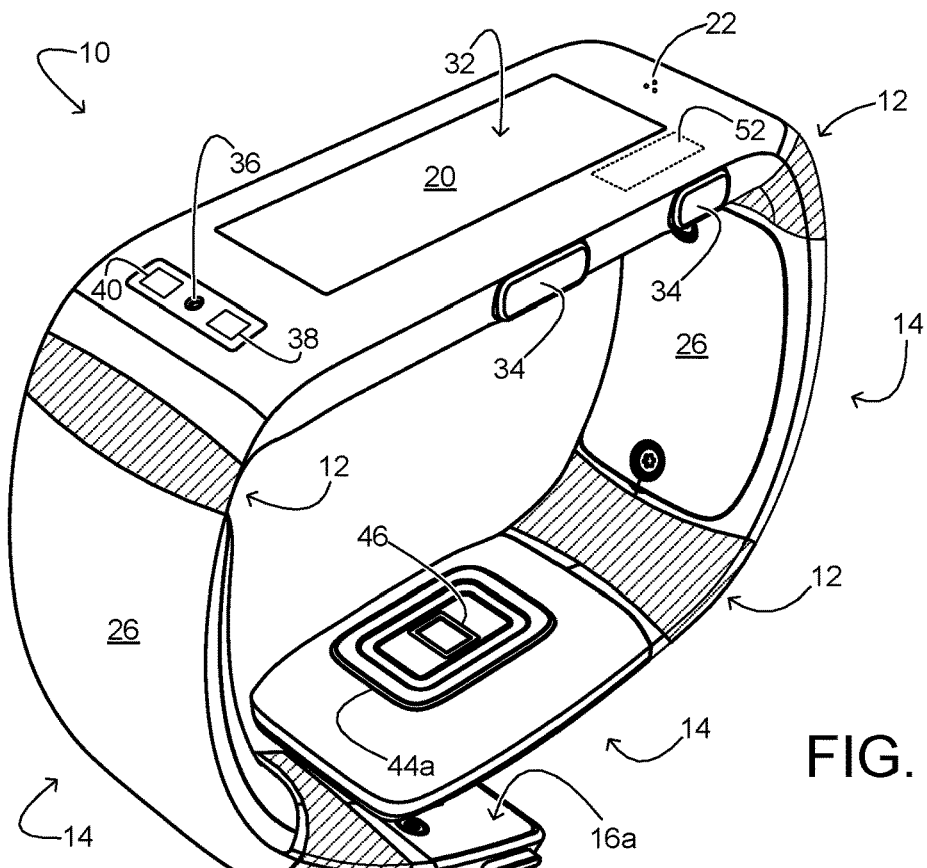
FIGS. 1A and 1B show a wearable heart rate monitoring device.
Figure 1B:
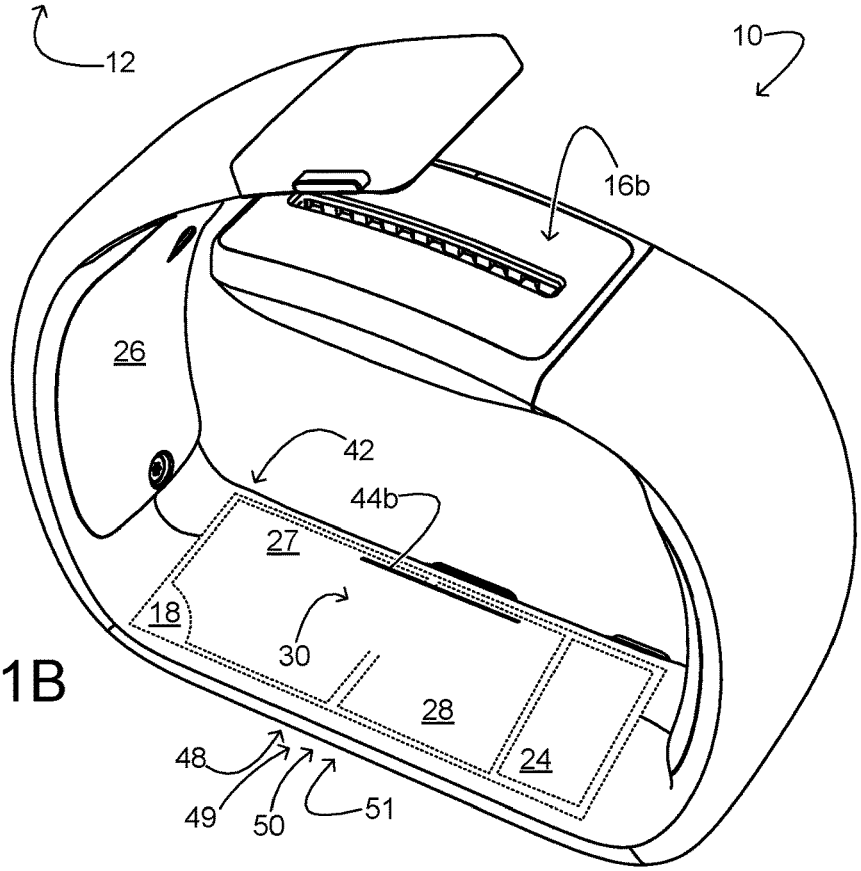

FIGS. 1A and 1B show aspects of an example sensory-and-logic system in the form of a wearable heart rate monitoring device 10, which may be usable to estimate a wearer's heart rate. The illustrated device is band-shaped and may be worn around a wrist. Device 10 includes at least four flexion regions 12 linking less flexible regions 14. The flexion regions of device 10 may be elastomeric in some examples. Fastening componentry 16A and 16B is arranged at both ends of the device. The flexion regions and fastening componentry enable the device to be closed into a loop and to be worn on a user's wrist. In other implementations, wearable heart rate monitoring devices of a more elongate band shape may be worn around the user's bicep, waist, chest, ankle, leg, head, or other body part. The device, for example, may take the form of eye glasses, a head band, an arm-band, an ankle band, a chest strap, or an implantable device to be implanted in tissue.

Wearable heart rate monitoring device 10 includes various functional components integrated into regions 14. In particular, the heart rate monitoring device includes a compute system 18, display 20, loudspeaker 22, communication suite 24, and various sensors. These components draw power from one or more energy-storage cells 26. A battery—e.g., a lithium ion battery—is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable heart rate monitoring device may include electro-mechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable heart rate monitoring device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. The compute system may include one or more hardware sensor interfaces configured to receive and interpret inputs from the various sensors. Such hardware sensor interfaces may receive inputs via electrical transmission over physical conductors (e.g., an electronic bus), light transmission over optical conveyances (e.g., fiber optics), electromagnetic signals conveyed over the air (e.g., radio frequency transmission), etc. Aspects of the compute system are described in further detail with reference to FIG. 7.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable heart rate monitoring device 10 and other computer systems, as well as providing recharge power. The communication suite may further include two-way Bluetooth, Wi-Fi, cellular, near-field communication and/or other radios. In some implementations, the communication suite may include an additional transceiver for optical, line-of-sight (e.g., infrared) communication.

In wearable heart rate monitoring device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, etc.

FIGS. 1A and 1B show various other sensors of wearable heart rate monitoring device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

FIGS. 1A and 1B show a pair of contact sensor modules 44A and 44B, which contact the wearer's skin when wearable heart rate monitoring device 10 is worn. The contact sensor modules may include independent or cooperating sensor elements, to provide a plurality of sensory functions. For example, the contact sensor modules may provide an electrical resistance and/or capacitance sensory function, which measures the electrical resistance and/or capacitance of the wearer's skin Compute system 18 may use such input to assess whether or not the device is being worn, for instance. In some implementations, the sensory function may be used to determine how tightly the wearable heart rate monitoring device is being worn. In the illustrated configuration, the separation between the two contact-sensor modules provides a relatively long electrical path length, for more accurate measurement of skin resistance. In some examples, a contact sensor module may also provide measurement of the wearer's skin temperature. Arranged inside contact sensor module 44B in the illustrated configuration is the optical heart rate sensor 46. The optical heart rate sensor may include an optical source and matched optical sensor to detect blood flow through the capillaries in the skin and thereby provide a measurement of the wearer's heart rate, blood oxygen level, blood glucose level, or other biomarkers with optical properties. Further details regarding the optical heart rate sensor, optical source, and optical sensor are provided with reference to FIG. 2.

Wearable heart rate monitoring device 10 may also include motion sensing componentry, such as an accelerometer 48, barometer 49, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The barometer may estimate a current elevation of the wearable heart rate monitoring device by evaluating local environmental barometric pressure. The wearable heart rate monitoring device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable heart rate monitoring device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable heart rate monitoring device, and only non-personal, summary data transmitted to the remote system.

Figure 2:
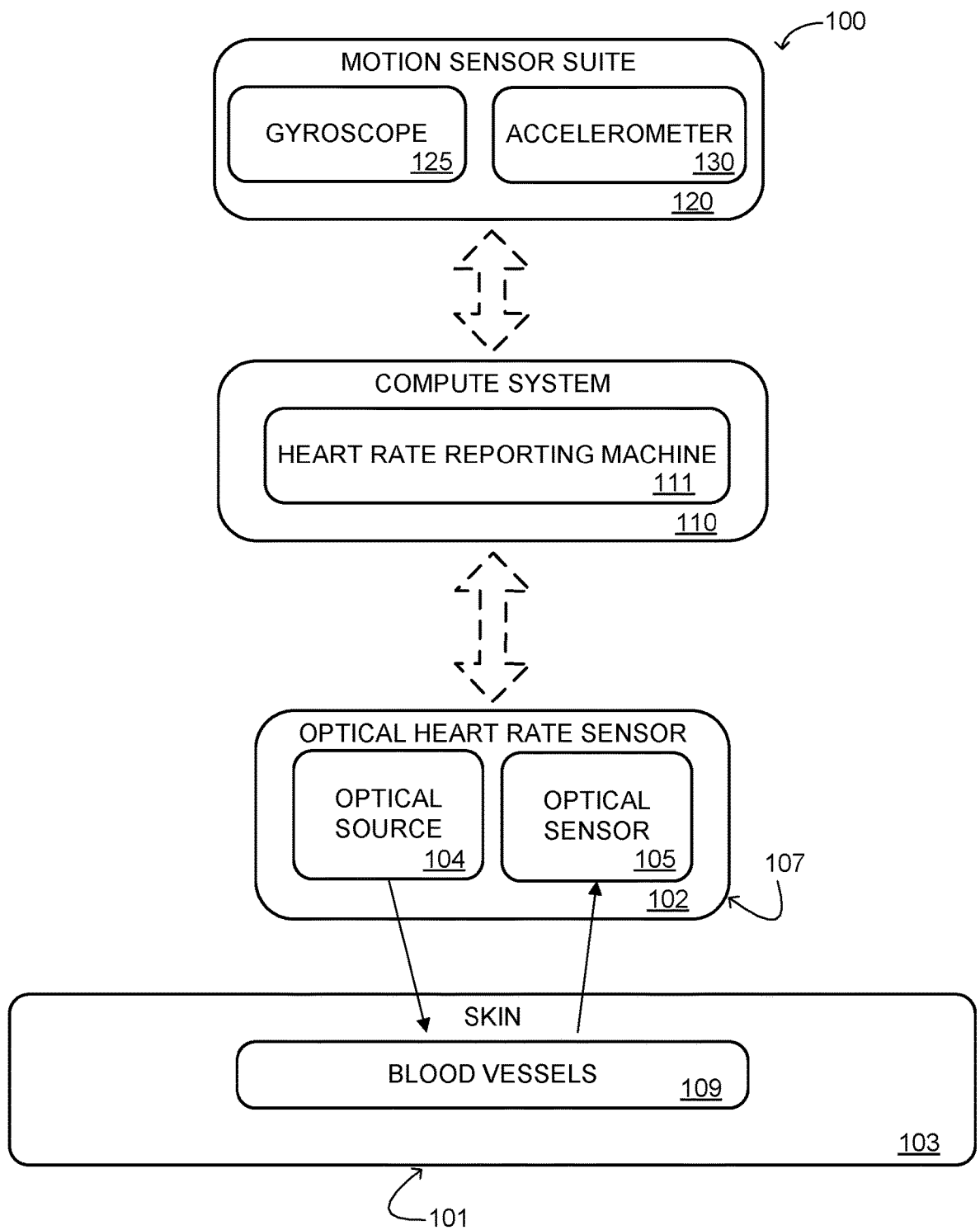
FIG. 2 schematically shows an example optical heart rate sensor that may be included in the wearable heart rate monitoring device of FIGS. 1A-1B.

FIG. 2 shows a schematic depiction of a sensory-and-logic system 100 coupled to the wrist of a wearer 101 so that an optical heart rate sensor 102 is adjacent to the skin 103 of wearer 101. Optical heart rate sensor 102 comprises an optical source 104 configured to illuminate with a test light one or more blood vessels through the skin of the wearer, and an optical sensor 105, configured to measure reflected test light from the blood vessels, thus comprising a photoplethysmogram (PPG) sensor. Optical source 104 may comprise one or more LED emitters, for example, while optical sensor 105 may comprise one or more photodiodes matched to detect light at frequencies that are based on the frequencies of light output by the optical source. Optical heart rate sensor 102 may be coupled within a housing 107 configured to promote contact between sensor 102 and skin 103, and further configured to block, filter, or otherwise limit ambient light from reaching the optical sensor. In this way, the majority of light reaching optical sensor 105 may be light originating from optical source 104 that has reflected off of blood vessels 109 beneath skin 103. As an example, FIG. 1A shows a wearable heart rate monitoring device 10 that is configured to position optical heart rate sensor 46 such that its optical source may illuminate capillaries located beneath the skin of the wearer's forearm while the wearable heart rate monitoring device is worn by the wearer. In other configurations, an optical heart rate sensor may be positioned within a wearable heart rate monitoring device such that an optical source illuminates a radial artery through the skin of the wearer while the wearable heart rate monitoring device is worn by the wearer. Alternatively, an optical heart rate sensor and its associated compute system may be housed separately and configured to communicate via a communication suite. For example, an optical heart rate sensor may be included in a head set and configured to illuminate capillaries located in the wearer's ear lobe while the head set is worn by the wearer, while the compute system resides within a wrist-worn computing device configured to communicate with the head set, via wireless communication, for example. An optical sensor may be configured to sense light reflected off of blood vessels located beneath the skin of the wearer (e.g., wrist worn), or the optical sensor may be configured to sense light transmitted through blood vessels located beneath the skin of the user (e.g., ear worn).

Compute system 110 may comprise heart rate reporting machine 111. Heart rate reporting machine 111 may provide control signals to optical source 104 and optical sensor 105. Heart rate reporting machine 111 may receive raw signals from optical sensor 105, and may further process the raw signals to a machine-readable heart rate signal, usable to determine heart rate, caloric expenditures, etc., as well as perform other operations including estimating a first candidate heart rate, comparing the first candidate heart rate to a machine-readable activity-strain signal, estimating a second candidate heart rate, and outputting one or more estimated heart rate values for additional processing and/or display to the wearer. Processed signals may be stored and output via the heart rate reporting machine, and/or other components of compute system 110. Control signals sent to optical source 104 and optical sensor 105 may be based on signals received from optical sensor 105, one or more motion sensors, ambient light sensors, information stored in compute system 110, input signals, etc.

The signal from the optical sensor may degrade in quality with increased motion, as wearer motion may change the optical properties of the skin, tissues, and blood vessels beneath the optical sensor. Further, wearer motion may impact the movement of blood and other fluids through the user's tissue. As such, the signal output by the optical sensor may need to be filtered or otherwise adjusted based on wearer movement prior to determining a heart rate of the wearer. Sensory-and-logic system 100 may include a motion sensor suite 120 communicatively coupled to compute system 110. Signals from motion sensor suite 120 may be provided to heart rate reporting machine 111. Motion sensor suite 120 may include gyroscope 125 and accelerometer 130. Gyroscope 125 and accelerometer 130 may be three-axis motion sensors. Accordingly, gyroscope 125 and accelerometer 130 may record and transmit signal channels for each axis.

A machine-readable heart rate signal S_P output by an optical sensor may be corrected to account for increased motion via a variety of suitable methods. In particular, one or more motion sensors of a wearable heart rate monitoring device may determine a motion signal, S_A, corresponding to a motion of the wearable heart rate monitoring device. The one or more motion sensors may comprise a gyroscope and/or an accelerometer, as nonlimiting examples. The gyroscope and/or accelerometer may be three-axis motion sensors. In those examples, the motion signal S_A output by the motion sensor may comprise a signal channel for each axis. As an example, a motion signal S_A may be received from the one or more motion sensors, and a motion frequency MA may be estimated based on the motion signal S_A.

After estimating the motion frequency MA, the motion frequency MA may be filtered from the machine-readable heart rate signal S_P, resulting in a motion-corrected heart rate signal IS. Filtering the machine-readable heart rate signal S_P based on the motion frequency MA may include applying a comb filter to the PPG signal, although other types of filters or methods of signal processing may be used to remove the motion frequency from the heart rate signal in addition to or as an alternative to the comb filter, such as infinite impulse response filters or notch filters.

After motion-correction, a first candidate wearer heart rate (HR) may be estimated via a first estimation approach based on a time domain representation of the motion-corrected heart rate signal IS. The motion-corrected heart rate signal IS may be analyzed in real time. As a non-limiting example, the motion-corrected heart rate signal S_P' may be detrended (i.e., a mean or best fit line subtracted from the machine-readable heart rate signal). A first candidate heart rate frequency HR may then be estimated based on zero-crossing events of the detrended filtered optical signal. A zero-axis may be determined and applied to the detrended filtered optical signal. Each heart beat comprises two zero-crossing events, a negative-to-positive zero-crossing event, and a positive-to-negative zero-crossing event. As such, the average length of time between alternating zero-crossing events may be used to estimate the first candidate heart rate. In some examples, the first candidate heart rate may be estimated based on amplitude peaks in addition to or as an alternative to zero crossing events. The length of time between consecutive amplitude peaks may be used to estimate the first candidate heart rate of the wearer. Other methods of estimating heart rate from a processed optical signal may be used in addition to or as an alternative to the described methods without departing from the scope of this disclosure.

Further, a series of heart rates estimated over a period of time may be averaged, resulting in a mean heart rate. Then, newly estimated heart rate values may be compared to the calculated mean heart rate. If newly estimated heart rate values deviate from the mean heart rate, they may be discarded as outliers and not reported to the wearer. This may serve to prevent acute signal contamination from affecting a recorded heart rate. For example, if a wearer of an electronic device suddenly stumbles and falls, the sudden motion may contaminate the machine-readable heart rate signal, leading the wearable heart rate monitoring device to estimate a first candidate heart rate which differs significantly from the wearer's actual heart rate. Comparing this estimated heart rate to the mean heart rate may result in the estimated heart rate being properly identified as an outlier, and discarded. Rather than report the erroneous estimated heart rate, the wearable heart rate monitoring device may continue to report the calculated mean heart rate, which in this example is more likely to match the wearer's actual heart rate.

Figure 3:
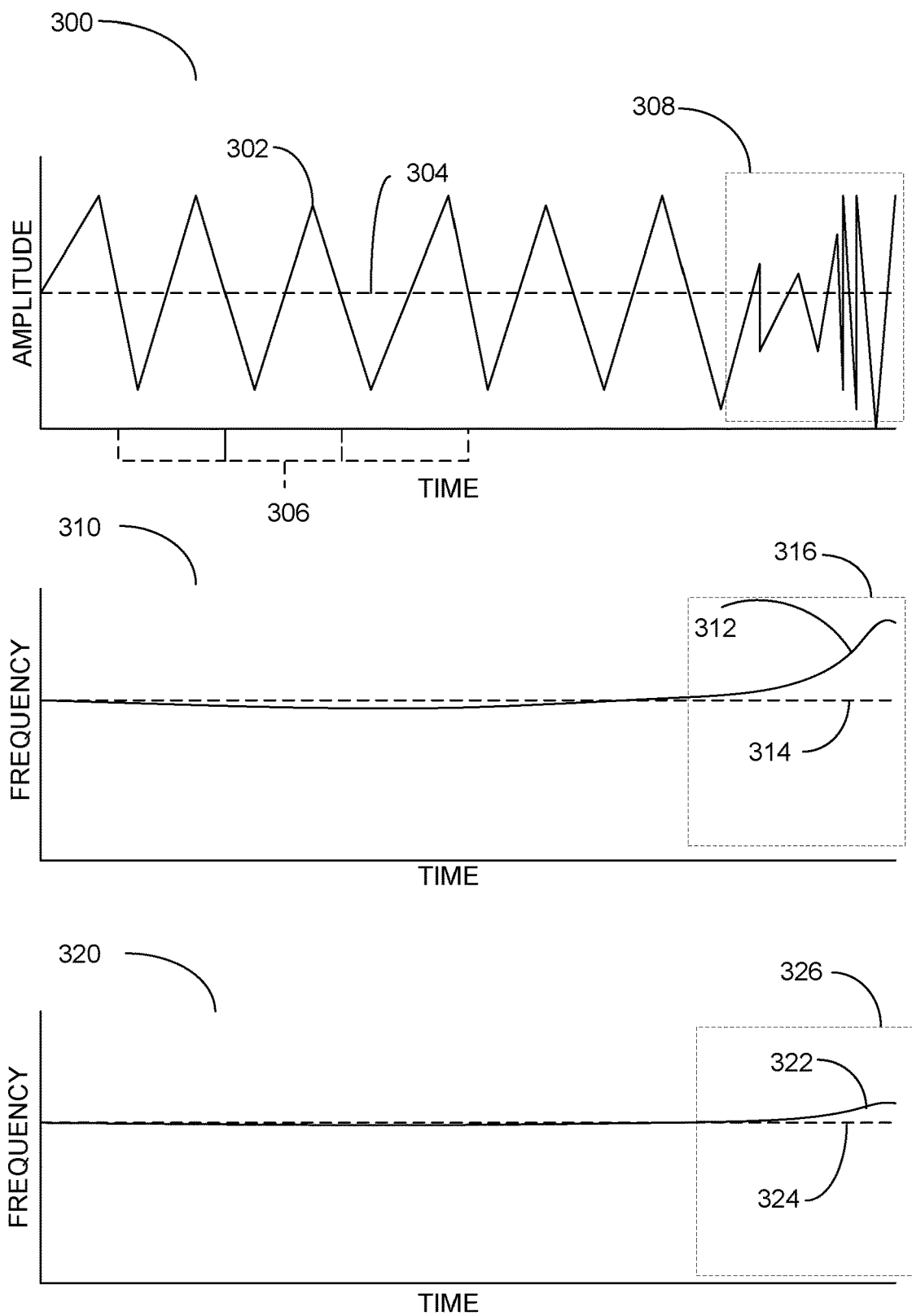
FIG. 3 illustrates heart rate estimation through discarding of outliers.

FIG. 3 illustrates the process described above. FIG. 3 includes graph 300, which shows a plot 302 of the amplitude of a time domain representation of a machine-readable heart rate signal measured by an optical sensor. Graph 300 also includes zero-axis 304, applied as described above. A first candidate heart rate may be estimated from graph 300 by calculating the distance between zero-axis crossing events, where each heart beat is defined by two crossings of the zero-axis. Intervals 306 show the approximate duration of each heart beat of a sample of heart beats near the beginning of the interval of time depicted in graph 300. The lengths of intervals 306 may be averaged, and used to calculate a mean heart rate. Within window 308, the shape of plot 302 becomes erratic. This may be the result of noise contamination of the PPG signal, as described above. For example, window 308 could indicate a moment when the wearer of the heart rate monitoring device stumbled and fell, introducing motion contamination into the machine-readable heart rate signal. As such, plot 302 within window 308 may not be an accurate representation of the heart rate of the wearer of the wearable heart rate monitoring device.

FIG. 3 also includes graph 310. Graph 310 shows a plot 312 of a wearer's heart rate frequency over time, as estimated from plot 302 of graph 300. Graph 310 additionally includes line 314, which indicates a calculated mean heart rate. Within window 316, plot 312 deviates significantly from line 314, suggesting a sudden change in heart rate. However, this deviation may be the result of noise contamination of the PPG signal shown within graph 300. Accordingly, the estimated heart rate shown within window 316 may not accurately reflect the actual heart rate of the wearer of the wearable heart rate monitoring device.

Similar to graph 310, graph 320 includes a plot 322 of a wearer's heart rate frequency over time, as estimated from plot 302 of graph 300. Graph 320 further includes line 324, which indicates a calculated mean heart rate. However, in contrast to graph 310, graph 320 was prepared by comparing new estimated heart rate values to the calculated mean heart rate, and discarding outliers. As a result, the estimated heart rate deviates from the calculated mean heart rate only slightly within window 326. Accordingly, the estimated heart rate shown within graph 320 may be more consistent with the actual heart rate of the wearer of the electronic device than the estimated heart rate shown in graph 310, as graph 320 is less affected by the sudden signal contamination present in window 308 of graph 300.

However, in some cases, discarding estimated heart rate values which deviate from a calculated mean heart rate, as shown in FIG. 3, may not facilitate the accurate estimation of a wearer's actual heart rate. For example, during elevation changes associated with physical activity, a wearer's actual heart rate may rapidly change from a previously calculated mean heart rate (e.g., the wearer's heart rate increases rapidly when climbing uphill). As a result, accurate estimates of the wearer's heart rate may be discarded as outliers, and the wearable heart rate monitoring device may erroneously report the wearer's heart rate as matching the previously calculated mean.

Accordingly, it may in some cases be desirable to take into account a machine-readable activity-strain signal when estimating wearer heart rate. The machine-readable activity-strain signal may in some examples be received from an elevation sensor, such as barometer 49 shown in FIG. 1B. In such an example, the elevation sensor may translate the elevation of the wearable heart rate monitoring device into a machine-readable elevation signal. Additionally or alternatively, the machine-readable activity-strain signal may indicate velocity, power, work, and/or energy as calculated by and received from an exercise machine, such as an exercise bike, rowing machine, weightlifting machine, etc.; one or more sensors configured to track physiological parameters of the wearer, such as respiration rate, footfall frequency, skin temperature, etc.; one or more input devices of the wearable heart rate monitoring device (e.g., the wearer may interact with physical buttons/switches/interfaces in order to indicate activity-strain); as well as any other suitable sources of activity-strain information.

After performing motion-correction on the machine-readable heart rate signal, and estimating the first candidate heart rate as described above, the first candidate heart rate may be compared to the machine-readable activity-strain signal in order to determine whether the first candidate heart rate is consistent with the machine-readable activity-strain signal. When the machine-readable activity-strain signal includes a machine-readable elevation signal, this may include evaluating any recent changes in elevation of the wearer of the wearable heart rate monitoring device.

For example, if it is determined that the wearable heart rate monitoring device has been gaining elevation for at least a threshold period of time, then the first candidate heart rate may be compared to an elevation gain threshold. If the first candidate heart rate is found to be lower than the threshold, and the wearable heart rate monitoring device has been gaining elevation for more than a threshold period of time, then the first candidate heart rate may be determined to be inconsistent with the machine-readable activity-strain signal. Otherwise, the first candidate heart rate may be determined to be consistent with the machine-readable activity-strain signal and output for additional processing and/or display to the wearer. Estimated heart rate values below the elevation gain threshold may be unlikely to correspond to an actual heart rate of a wearer of a wearable heart rate monitoring device who has been performing the relatively taxing activity of climbing uphill for a significant period of time. The elevation gain threshold and the threshold period of time may be any suitable values. In some examples, the elevation gain threshold may be 90 beats per minute (bpm).

Additionally or alternatively the wearable heart rate monitoring device may check whether the first candidate heart rate is significantly lower than a calculated mean heart rate. For example, the wearable heart rate monitoring device may determine whether the first candidate heart rate is less than the mean heart rate by more than an elevation gain disparity threshold. When performing the relatively taxing activity of climbing uphill, it is unlikely that the heart rate of a wearer of a wearable heart rate monitoring device will decrease significantly. As a result, if the first candidate heart rate is less than the mean heart rate by more than the elevation gain disparity threshold, then it may be determined that the first candidate heart rate is inconsistent with the machine-readable activity-strain signal. Otherwise, the first candidate heart rate may be determined to be consistent with the machine-readable activity-strain signal, and output for further processing and/or display to the wearer. In some examples, the elevation gain disparity threshold may be equal to 10 bpm.

Additionally or alternatively, if it is determined that the wearable heart rate monitoring device is moving downhill or not changing in elevation, then the wearable heart rate monitoring device may check whether the first candidate heart rate is significantly higher than the mean heart rate. This may involve determining whether the first candidate heart rate is more than the mean heart rate by at least an elevation loss disparity threshold. While performing the relatively less taxing activity of moving downhill or moving at a constant rate on a flat surface, it is unlikely that a wearer's heart rate will increase significantly. As a result, if the first candidate heart rate is more than the mean heart rate by more than the elevation loss disparity threshold, it may be determined that the first candidate heart rate is inconsistent with the machine-readable activity-strain signal. Otherwise, the first candidate heart rate may be determined to be consistent with the machine-readable activity-strain signal, and output for further processing and/or display to the wearer. In some examples, the elevation loss disparity threshold may be equal to 25 bpm.

Based on at least determining that the first candidate heart rate is inconsistent with the machine-readable activity-strain signal, the wearable heart rate monitoring device may estimate and output a second candidate heart rate using a second estimation approach, which differs from the first estimation approach described above. The second estimation approach may include identifying a highest occurrence frequency (e.g., in beats per minute) in a frequency search window of a frequency domain representation of the machine-readable heart rate signal. The frequency search window may be centered on the mean heart rate, and have any suitable range (e.g., 10 bpm, 20 bpm, or 30 bpm). The highest occurrence frequency identified within the frequency search window may be selected as the second heart rate candidate and output for further processing and/or display to the wearer.

In examples where the machine-readable activity-strain signal is not received from an elevation sensor, alternative assessments may be performed in order to determine whether the first candidate heart rate is consistent with the machine-readable activity-strain signal. For example, in the event that the machine-readable activity-strain signal indicates that the wearer has recently increased velocity, power, work, and/or any other parameter positively correlated to energy expenditure (e.g., begun performing a repetitive motion with an increased frequency or begun moving/lifting heavier weight) appropriate alternative calculations may be performed in order to assess whether the first candidate heart rate is consistent with the activity-strain signal. Further, calculations may be performed which attempt to account for multiple strain indications simultaneously. For example, a user may transition from running along a flat surface to walking uphill. In general, any series of calculations may be performed in order to determine whether a first candidate heart rate is consistent with a variety of different strain indicators, both alone and in combination.

Figure 4:
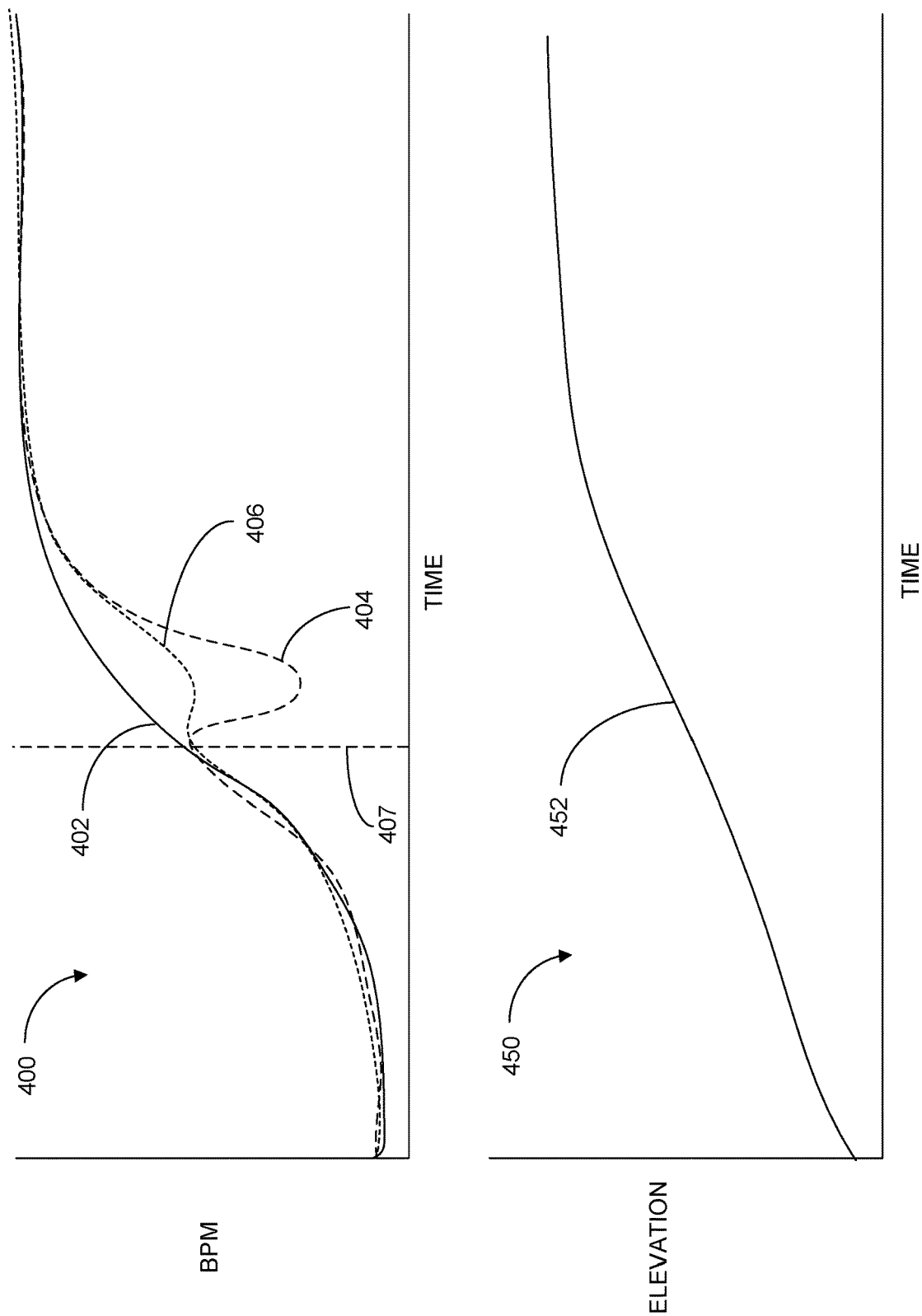
FIG. 4 shows a graph of a wearer's actual heart rate, mean heart rate, and first candidate heart rate over time.

FIG. 4 shows a graph 400 of the heart rate of a wearer of a wearable heart rate monitoring device. In particular, graph 400 includes plot 402, indicating the wearer's actual heart rate over time, plot 404, indicating the estimated first candidate heart rate over time, and plot 406, indicating the estimated second candidate heart rate over time. FIG. 4 also shows a graph 450 including plot 452, which indicates the output of an elevation sensor over time Plot 452 may therefore represent a machine-readable activity-strain signal/elevation signal.

As shown, the wearable heart rate monitoring device gradually gains elevation over the duration of the time interval shown in graph 450. The wearer's heart rate 402 gradually increases as the wearer performs the relatively taxing activity of walking uphill. Initially, both the first and second candidate heart rates are relatively close to the actual heart rate. However, at time indicator 407, first candidate heart rate 404 sharply diverges from the actual heart rate. This may occur when the wearer's actual heart rate is similar to the wearer's motion frequency, causing the heart rate signal to be improperly filtered during motion correction. In such a situation, the wearable heart rate monitoring device may determine that the first candidate heart rate is inconsistent with the machine-readable activity-strain signal, given that a wearer's heart rate will not typically decrease abruptly when the wearer is walking uphill. Instead, the wearable heart rate monitoring device may output the second candidate heart rate. As described above, the second candidate heart rate may be based at least in part on the calculated mean heart rate, rendering it less susceptible to acute contamination of the heart rate signal. This is illustrated in FIG. 4, as the second candidate heart rate is significantly more accurate than the first candidate heart rate immediately after time indicator 407.

Figure 5:
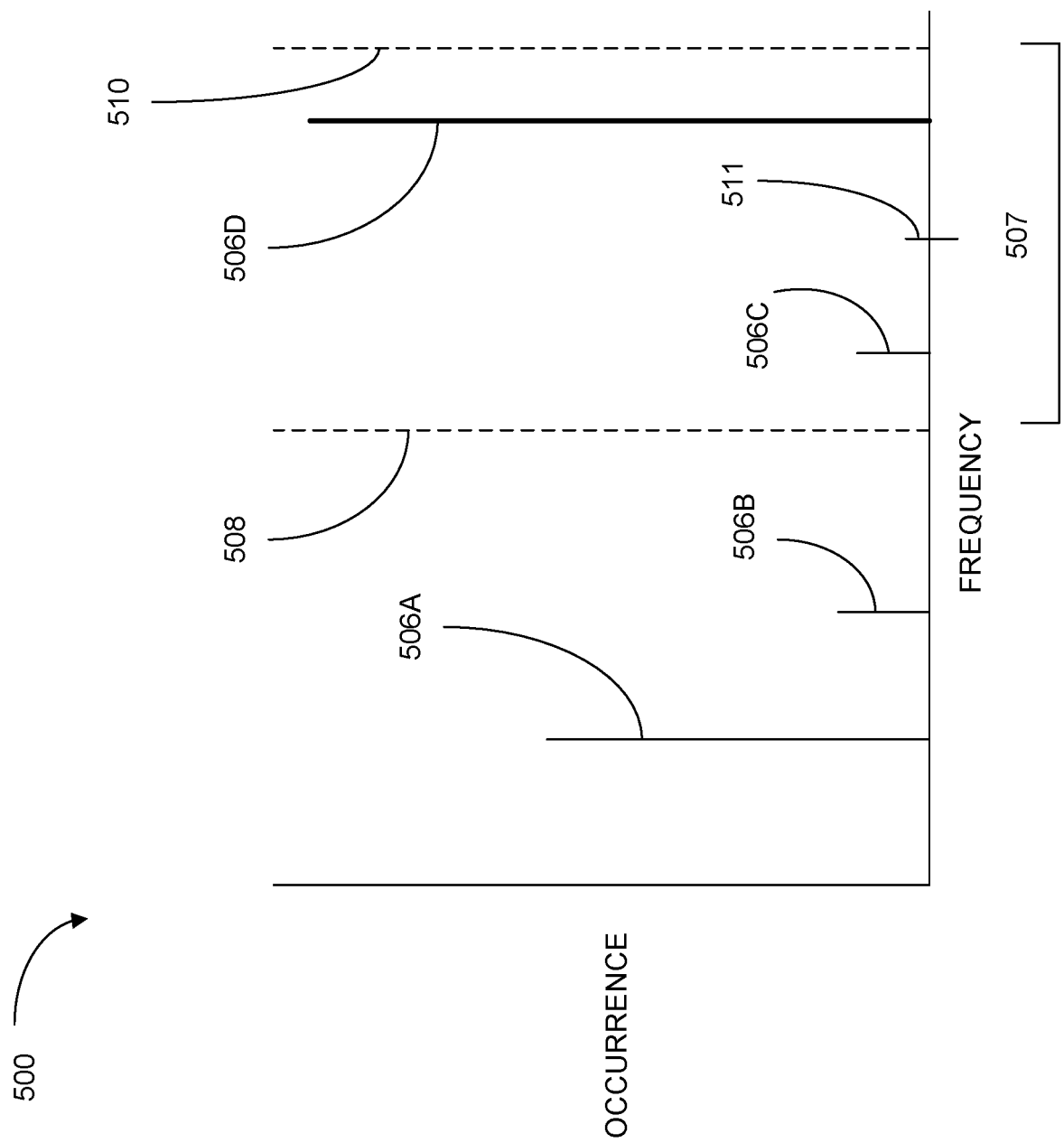
FIG. 5 shows a frequency domain representation of a machine-readable heart rate signal.

As described above, under some circumstances it may be determined that the first candidate heart rate is inconsistent with the machine-readable activity-strain signal. As a result, the wearable heart rate monitoring device may utilize a second estimation approach, which may include identifying a highest occurrence frequency in a frequency search window of a frequency domain representation of a machine-readable heart rate signal. As an example, plot 406 of FIG. 4 shows the results of this approach and FIG. 5 shows an example of using this approach. In particular, FIG. 5 shows a frequency domain representation 500 of a machine-readable heart rate signal. Representation 500 includes a number of frequency peaks 506, where a height of each frequency peak indicates the relative occurrence of each represented frequency in the machine-readable heart rate signal. In representation 500, frequency peak 506D has been identified as representing the highest occurrence frequency in the frequency domain representation of the machine-readable heart rate signal. Accordingly, the frequency represented by frequency peak 506D may be selected as the highest occurrence frequency, and output as the second candidate heart rate. Representation 500 also includes a frequency search window 507. Frequency search window 507 is defined by a lower bound 508 and an upper bound 510. Only frequencies located within the frequency search window may be considered as potential heart rate candidates. As described above, the range of search window 507, as well as the positions of lower bound 508 and upper bound 510, may vary according to a variety of factors, including wearer motion frequency and activity type. Alternatively, frequency search window 507 may have a fixed range, and be centered on a calculated mean heart rate frequency 511.

Figure 6:
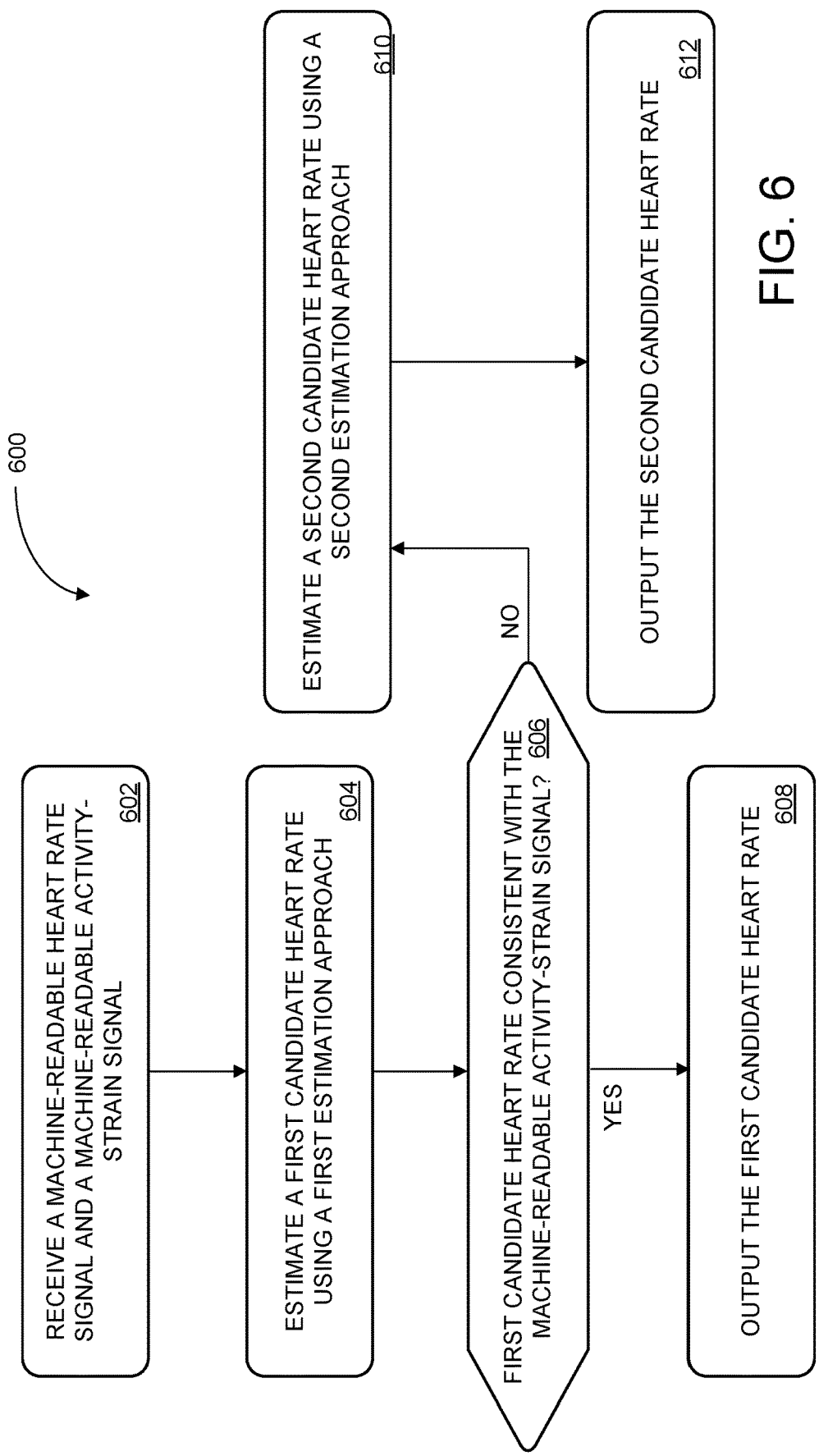
FIG. 6 illustrates an example method for estimating heart rate.

FIG. 6 schematically shows an example method 600 for monitoring wearer heart rate. At 602 method 600 includes receiving a machine-readable heart rate signal and a machine-readable activity-strain signal. As described above, the machine-readable activity-strain signal may be received from an elevation sensor and comprise a machine-readable elevation signal. Additionally or alternatively the machine-readable activity-strain signal may be received from an exercise machine, one or more sensors configured to track wearer physiological parameters, etc.

At 604 method 600 includes estimating a first candidate heart rate using a first estimation approach. The first heart rate estimation approach may include motion-correcting the machine-readable heart rate signal to a motion-corrected heart rate signal and estimating the first candidate heart rate by evaluating an average length of time between crossings of the zero-axis by the motion-corrected heart rate signal.

At 606 method 600 includes determining whether the first candidate heart rate is consistent with the machine-readable activity-strain signal. If yes, method 600 proceeds to step 608, which includes outputting the first candidate heart rate for further processing and/or display to the wearer. If no, method 600 proceeds to step 610, which includes estimating a second candidate using a second heart rate estimation approach. The second heart rate estimation approach may include identifying a highest occurrence frequency in a frequency search window of the machine-readable heart rate signal. The frequency search window may be centered on a calculated mean heart rate of the wearer.

At 612, method 600 includes outputting the second candidate heart rate for further processing and/or display to the wearer.

In some embodiments, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 7.

Figure 7:
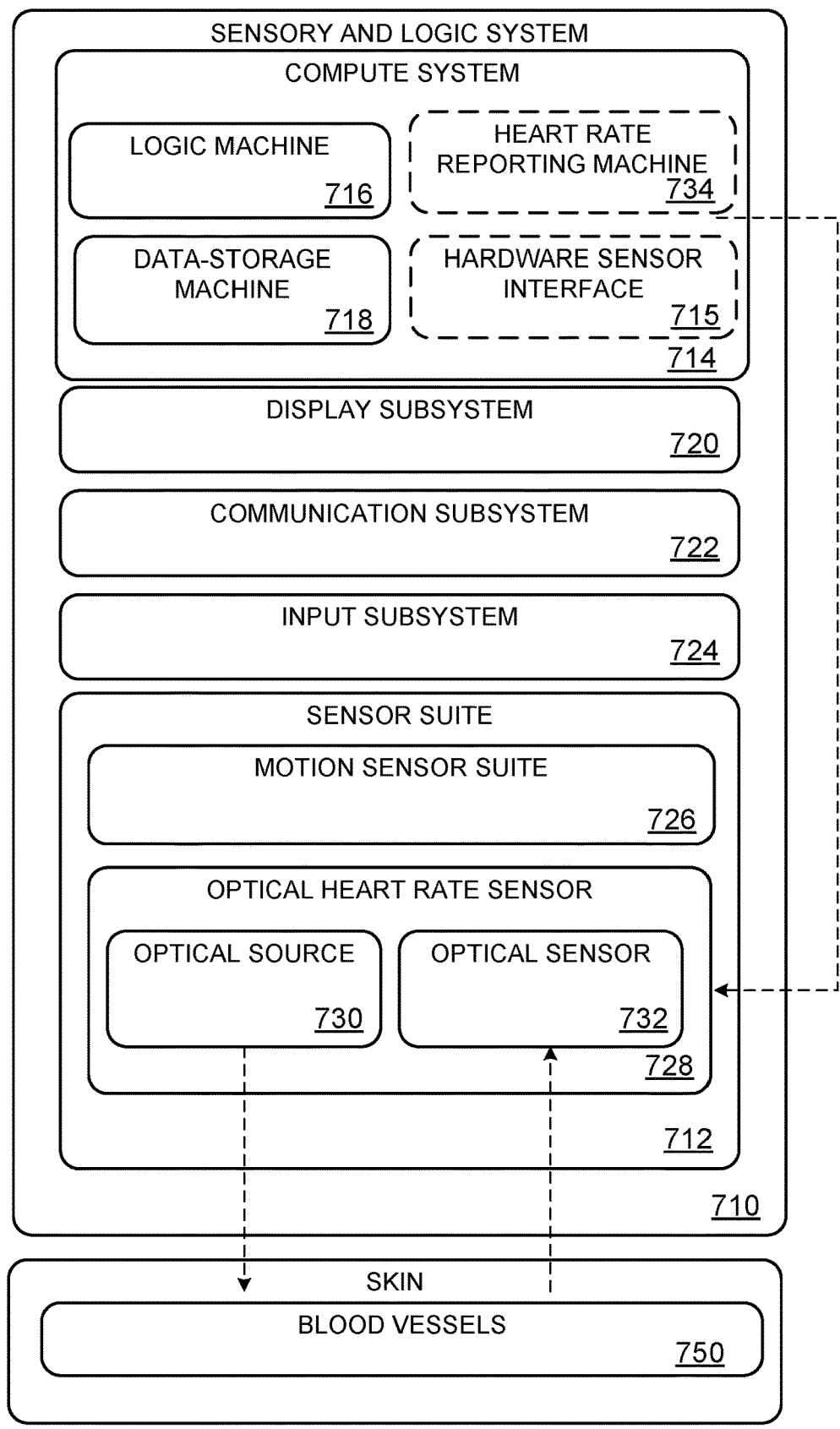
FIG. 7 schematically shows an example computing system

FIG. 7 schematically shows a form-agnostic sensory-and-logic system 710 that includes a sensor suite 712 operatively coupled to a compute system 714. The compute system may include one or more hardware sensor interfaces 715 configured to receive inputs from sensors included in sensor suite 712. The compute system includes a logic machine 716 and a data-storage machine 718. The compute system is operatively coupled to a display subsystem 720, a communication subsystem 722, an input subsystem 724, and/or other components not shown in FIG. 7.

Logic machine 716 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 716 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 718 includes one or more physical devices configured to hold instructions executable by logic machine 716 to implement the methods and processes described herein. When such methods and processes are implemented, the state of the data-storage machine may be transformed e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 718 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 716 and data-storage machine 718 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 720 may be used to present a visual representation of data held by data-storage machine 718. This visual representation may take the form of a graphical user interface (GUI). As the herein described methods and processes change the data held by the storage machine, and thus transform the state of the storage machine, the state of display subsystem 720 may likewise be transformed to visually represent changes in the underlying data. Display subsystem 720 may include one or more display subsystem devices utilizing virtually any type of technology. Such display subsystem devices may be combined with logic machine 716 and/or data-storage machine 718 in a shared enclosure, or such display subsystem devices may be peripheral display subsystem devices. Display 20 of FIGS. 1A and 1B is an example of display subsystem 820.

Communication subsystem 722 may be configured to communicatively couple compute system 714 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 822.

Input subsystem 724 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch-screen sensor 32 and push buttons 34 of FIGS. 1A and 1B are examples of input subsystem 724.

Sensor suite 712 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIGS. 1A and 1B. Sensor suite 712 may include motion sensor suite 726. Motion sensor suite 726 may include one or more of an accelerometer, gyroscope, magnetometer, barometer, and/or other suitable motion detectors. Sensor suite 712 may further include optical heart rate sensor 728. As described herein, optical heart rate sensor 728 may include optical source 730 and optical sensor 732. Optical source 730 may comprise one or more LED emitters, for example, while optical sensor 732 may comprise one or more photodiodes matched to detect light at frequencies that are based on the frequencies of light output by the optical source. Optical source 730 may be configured to illuminate one or more blood vessels 750 through the skin 752 of the wearer, and optical sensor 732 may be configured to measure illumination reflected from or transmitted through blood vessels 750.

Compute system 714 may include one or more hardware sensor interfaces 715, configured to receive and process inputs from sensors of the sensor suite. Further, compute system 714 may include a heart rate reporting machine 734, which may be integrated with and/or communicatively coupled to logic machine 716 and data-storage machine 718 and perform one or more of the heart rate estimation, evaluation, and output processes described above. Heart rate reporting machine 734 may receive raw signals from optical sensor 732, and may further process the raw signals to determine heart rate, caloric expenditures, etc. Processed signals may be stored and output via compute system 714. Control signals sent to optical source 730 and optical sensor 732 may be based on signals received from optical sensor 732, signals derived from sensor suite 712, information stored in data-storage machine 718, input received from communication subsystem 722, input received from input subsystem 724, etc.

In an example, a computing device comprises: a hardware sensor interface configured to receive a machine-readable heart rate signal and a machine-readable activity-strain signal indicating relative strenuousness of an activity performed by a wearer of the computing device; and a heart rate reporting machine configured to: estimate a first candidate heart rate of the wearer based on the machine-readable heart rate signal using a first heart rate estimation approach; and based on at least determining that the first candidate heart rate of the wearer is consistent with the machine-readable activity-strain signal, output the first candidate heart rate; or based on at least determining that the first candidate heart rate of the wearer is inconsistent with the machine-readable activity-strain signal, output a second candidate heart rate of the wearer based on the machine-readable heart rate signal using a second heart rate estimation approach different than the first heart-rate estimation approach. In this example or any other example, the first heart rate estimation approach includes: motion-correcting the machine-readable heart rate signal to a motion-corrected heart rate signal; and estimating the first candidate heart rate by evaluating an average length of time between crossings of a zero-axis by the motion-corrected heart rate signal. In this example or any other example, the second heart rate estimation approach includes identifying a highest occurrence frequency in a frequency search window of a frequency domain representation of the machine-readable heart rate signal. In this example or any other example, the frequency search window is centered on a calculated mean heart rate of the wearer. In this example or any other example, the machine-readable activity-strain signal indicates elevation and is received from an elevation sensor. In this example or any other example, the first candidate heart rate is determined to be inconsistent with the machine-readable activity-strain signal based on at least determining that the computing device has been gaining elevation for at least a threshold period of time, and the first candidate heart rate is lower than an elevation gain threshold. In this example or any other example, the elevation gain threshold is equal to 90 beats per minute. In this example or any other example, the first candidate heart rate is determined to be inconsistent with the machine-readable activity-strain signal based on at least determining that the computing device has been gaining elevation for at least a threshold period of time, and the first candidate heart rate is lower than a calculated mean heart rate by more than an elevation gain disparity threshold. In this example or any other example, the elevation gain disparity threshold is equal to 10 beats per minute. In this example or any other example, the first candidate heart rate is determined to be inconsistent with the machine-readable activity-strain signal based on at least determining that the wearer is losing elevation or not changing in elevation, and the first candidate heart rate is higher than a calculated mean heart rate by more than an elevation loss disparity threshold. In this example or any other example, the elevation loss disparity threshold is equal to 25 beats per minute. In this example or any other example, the machine-readable activity-strain signal indicates one or more of velocity, power, work, or energy and is received from an exercise machine. In this example or any other example, the machine-readable activity-strain signal indicates a current respiration rate of the wearer.

In an example, a wearable heart rate monitoring device comprises: an optical sensor configured to translate test light reflected from a wearer of the wearable heart rate monitoring device into a machine-readable heart rate signal; an elevation sensor configured to translate an elevation of the wearable heart rate monitoring device into a machine-readable elevation signal; and a heart rate reporting machine configured to: estimate a first candidate heart rate of the wearer based on a time domain representation of the machine-readable heart rate signal; based on at least determining that the first candidate heart rate of the user is consistent with the machine-readable elevation signal, the first candidate heart rate is output; or based on at least determining that the first candidate heart rate of the user is inconsistent with the machine-readable elevation signal, a highest occurrence frequency in a frequency search window of a frequency domain representation of the machine-readable heart rate signal is identified and output as a second candidate heart rate value. In this example or any other example, estimating the first candidate heart rate includes: motion-correcting the time domain representation of the machine-readable heart rate signal to a motion-corrected heart rate signal; and estimating the first candidate heart rate by evaluating an average length of time between crossings of a zero-axis by the motion-corrected heart rate signal. In this example or any other example, the first candidate heart rate is determined to be inconsistent with the machine-readable elevation signal based on at least determining that the wearable heart rate monitoring device has been gaining elevation for at least a threshold period of time, and the first candidate heart rate is lower than an elevation gain threshold of 90 bpm. In this example or any other example, the first candidate heart rate is determined to be inconsistent with the machine-readable elevation signal based on at least determining that the wearable heart rate monitoring device has been gaining elevation for at least a threshold period of time, and the first candidate heart rate is lower than a calculated mean heart rate by more than an elevation gain disparity threshold of 10 bpm. In this example or any other example, the first candidate heart rate is determined to be inconsistent with the machine-readable elevation signal based on at least determining that the wearer is losing elevation or not changing in elevation, and the first candidate heart rate is higher than a calculated mean heart rate by more than an elevation loss disparity threshold of 25 bpm. In this example or any other example, the frequency search window is centered on a calculated mean heart rate of the wearer.

In an example, a wearable heart rate monitoring device comprises: an optical sensor configured to translate test light reflected from a wearer of the wearable heart rate monitoring device into a machine-readable heart rate signal; an elevation sensor configured to translate an elevation of the wearable heart rate monitoring device into a machine-readable elevation signal; and a heart rate reporting machine configured to output an estimated heart rate based on at least the machine-readable heart rate signal and the machine-readable elevation signal.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computing device, comprising:
   a hardware sensor interface configured to receive a machine-readable heart rate signal from a heart rate sensor and configured to receive a machine-readable activity-strain signal from an activity-strain sensor, the machine-readable activity-strain signal indicating relative strenuousness of an activity performed by a wearer of the computing device; and
   a heart rate reporting machine including a computer processor configured to:
      estimate a first candidate heart rate of the wearer based on the machine-readable heart rate signal by applying a first heart rate estimation approach to a time domain representation of the machine-readable heart rate signal;
      determine that the first candidate heart rate of the wearer, as previously estimated via the first heart rate estimation approach, is inconsistent with the relative strenuousness of the activity performed by the wearer of the computing device based on the machine-readable activity-strain signal; and
      output a second candidate heart rate of the wearer, the second candidate heart rate being different from the first candidate heart rate, by applying a second heart rate estimation approach different than the first heart rate estimation approach to a frequency domain representation of the same machine-readable heart rate signal used to previously estimate the first candidate heart rate via the first heart rate estimation approach.

2. The computing device of claim 1, where the first heart rate estimation approach includes:
   motion-correcting the time domain representation of the machine-readable heart rate signal to a motion-corrected heart rate signal; and
   estimating the first candidate heart rate by evaluating an average length of time between crossings of a zero-axis by the motion-corrected heart rate signal.

3. The computing device of claim 1, where the second heart rate estimation approach includes identifying a highest occurrence frequency in a frequency search window of the frequency domain representation of the machine-readable heart rate signal.

4. The computing device of claim 3, where the frequency search window is centered on a calculated mean heart rate of the wearer.

5. The computing device of claim 1, where the machine-readable activity-strain signal indicates elevation and the activity-strain sensor is an elevation sensor.

6. The computing device of claim 5, where the first candidate heart rate is determined to be inconsistent with the machine-readable activity-strain signal based on at least determining that the computing device has been gaining elevation for at least a threshold period of time, and the first candidate heart rate is lower than an elevation gain threshold.

7. The computing device of claim 6, where the elevation gain threshold is equal to 90 beats per minute.

8. The computing device of claim 5, where the first candidate heart rate is determined to be inconsistent with the relative strenuousness of the activity performed by the wearer of the computing device based on at least determining that the computing device has been gaining elevation for at least a threshold period of time, and the first candidate heart rate is lower than a calculated mean heart rate by more than an elevation gain disparity threshold.

9. The computing device of claim 8, where the elevation gain disparity threshold is equal to 10 beats per minute.

10. The computing device of claim 5, where the first candidate heart rate is determined to be inconsistent with the relative strenuousness of the activity performed by the wearer of the computing device based on at least determining that the wearer is losing elevation or not changing in elevation, and the first candidate heart rate is higher than a calculated mean heart rate by more than an elevation loss disparity threshold.

11. The computing device of claim 10, where the elevation loss disparity threshold is equal to 25 beats per minute.

12. The computing device of claim 1, where the machine-readable activity-strain signal indicates one or more of velocity, power, work, or energy and is received from an exercise machine.

13. The computing device of claim 1, where the machine-readable activity-strain signal indicates a current respiration rate of the wearer.

* * * * *